(12) United States Patent
Delatorre (10) Patent No.: US 8,356,509 B2
(45) Date of Patent: Jan. 22, 2013

(54) DIFFERENTIAL TORQUE DENSITOMETER

(76) Inventor: Leroy C. Delatorre, Sugar Land, TX (US)

( * ) Notice: Subject to any disclaimer, the term of this patent is extended or adjusted under 35 U.S.C. 154(b) by 385 days.

(21) Appl. No.: 12/803,593

(22) Filed: Jun. 30, 2010

(65) Prior Publication Data
US 2011/0000298 A1      Jan. 6, 2011

Related U.S. Application Data

(60) Provisional application No. 61/270,194, filed on Jul. 6, 2009.

(51) Int. Cl.
*G01N 9/16* (2006.01)
*G01N 9/20* (2006.01)

(52) U.S. Cl. .............. 73/32 R; 73/454; 73/440

(58) Field of Classification Search .......... 73/32 R, 73/433, 440, 447, 453, 454
See application file for complete search history.

(56) References Cited

U.S. PATENT DOCUMENTS

| | | | | |
|---|---|---|---|---|
| 3,783,693 A | * | 1/1974 | Paros | 73/701 |
| 3,812,767 A | * | 5/1974 | Prescott | 92/48 |
| 3,853,007 A | * | 12/1974 | Jaquith | 73/706 |
| 4,030,366 A | * | 6/1977 | Kazahaya et al. | 73/715 |
| 4,353,253 A | | 10/1982 | Callaghan | |
| 4,628,740 A | * | 12/1986 | Ueda et al. | 73/705 |
| 5,463,903 A | | 11/1995 | Delatorre | |
| 6,457,357 B1 | | 10/2002 | Stuart-Bruges | |
| 6,532,822 B1 | * | 3/2003 | Boyd | 73/702 |
| 6,601,461 B2 | * | 8/2003 | Maxit et al. | 73/861.79 |

FOREIGN PATENT DOCUMENTS

WO    WO 97/21077    6/1997

* cited by examiner

*Primary Examiner* — Helen C. Kwok
(74) *Attorney, Agent, or Firm* — W. Allen Marcontell (57) ABSTRACT

A densitometer suitable for fluid measurements in remote, hostile environments comprises one or more pairs of matched weight masses housed within a tube and having respectively different densities. When immersed in the subject fluid, the buoyancy differential between the masses is converted to a proportional torque oriented about an axis aligned substantially parallel with a pipe bore. The torque is transferred through a calibrated environmental isolation cylinder to an electric property sensor positioned in a protected environment. A proportionalized electric property signal is transmitted to a value reading station.

18 Claims, 7 Drawing Sheets

DIFFERENTIAL TORQUE DENSITOMETER

CROSS-REFERENCE TO RELATED APPLICATION

The priority date benefit of Provisional Application No. 61/270,194 titled Differential Torque Densitometer filed Jul. 6, 2009 is claimed for this application.

BACKGROUND OF THE INVENTION

1. Field of the Invention

This invention relates to a densitometer for measuring fluid density within an oil or gas well environment. Specifically, this environment will generally include exposure to high temperatures, high pressures, corrosive media, shock and vibration. Additional requirements are also a small diametrical size, low power consumption and the ability to make measurements while in motion.

2. Description of Related Prior Art

Fluid density within an oil or gas well has long been a very important parameter for well troubleshooting and evaluations. The most suitable instrument for this measurement has traditionally been based on nuclear radiation. Contemporary restrictions on the licensing and use of nuclear sources, however, have made this an increasingly unattractive approach.

Another substitute approach involves measuring the fluid head pressure differential between two points. This approach requires a differential pressure sensor capable of measuring very low pressure differences, in the presence of a potentially large static pressure. For example, the pressure head of water is one PSI for a height difference of about 27 inches. This must be accurately measured in the presence of, perhaps, 10,000 PSI static pressure. This is not only a difficult task but the high pressure environment can easily create opportunities for overpressure and destruction of the sensor.

It is an object of this invention, then, to provide a fluid density sensor suitable for making accurate density measurements within the conditions encountered in oil or gas wells.

SUMMARY OF THE INVENTION

This invention is designed to utilize Archimedes principle of buoyancy on two (or more) balanced, immersed bodies, arranged to create a differential torque proportional to fluid density. This balanced, differential structure is also optimized to reject the effects of shock, vibration and gravity (position orientation). Since the fluid density being measured is within a well bore, then the measurement must also be insensitive to the effects of high static pressures. Provision is also made to couple the differential torque, proportional to density, to an output shaft aligned with the axis of the pressure housing. It is further coupled from the well bore pressure into an instrument pressure housing environment by means of a torque pressure isolator tube.

A second embodiment utilizes two sets of immersion bodies, coupled together in a push-pull arrangement. Balancing is done by summing positive and negative torque values within a single shaft, which is aligned parallel to the pressure housing axis.

BRIEF DESCRIPTION OF THE DRAWINGS

The advantages and further features of the invention will be readily appreciated by those of ordinary skill in the art as the same becomes better understood by reference to the following detailed description when considered in conjunction with the accompanying drawings in which like reference characters designate like or similar elements throughout.

DESCRIPTION OF THE PREFERRED EMBODIMENTS

Figure 1:
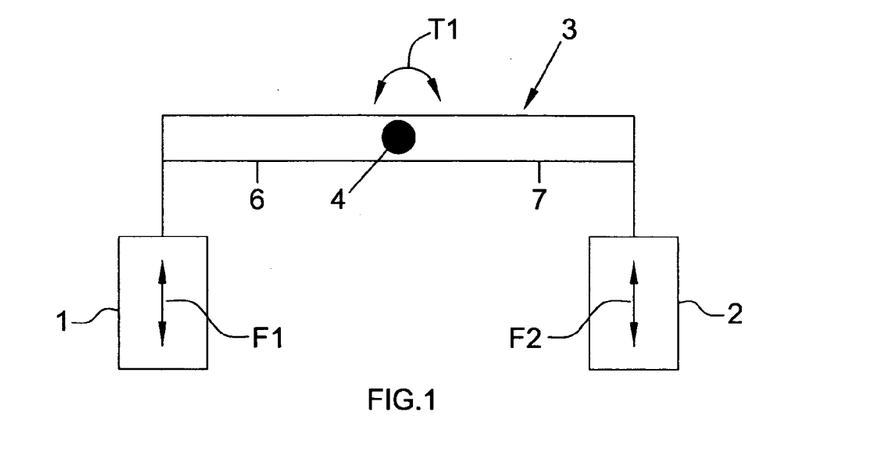
FIG. 1 is an illustration of two bodies configured as a balanced, differential pair.

FIG. 1 illustrates a pair of bodies, 1 and 2, which are balanced on a balance beam, 3. The balance beam is supported and pivoted by a torque shaft, 4, so that any imbalance will be converted to a proportional torque, 5, around the axis of this shaft. If bodies 1 and 2 are identical and the balance beam moment arms, 6 and 7 are identical, forces, F1 and F2, will also be identical and no torque will be generated by gravity (the weight of the bodies). This condition also will not generate any torque if both bodies are immersed within a fluid since the buoyancies of both bodies are equal.

Suppose, however, that body, 1, were to be made of a much lower density material than body 2. Gravity balance, for this situation, will be maintained if body, 1, is made larger so that its total mass is equal to that of body 2. Buoyancy, though, is no longer equal for the two bodies because their volumes are now different and Archimedes principle states that the buoyant force of a body is equal to the weight of the fluid it displaces. Body, 1, is now larger so it will have a greater buoyant force than body, 2. Gravity, and other common acceleration forces, continue to be balanced out but immersion in a fluid will now generate a torque proportional to fluid density.

The magnitude of this effect cannot be altered by changing the ratio of the balance beam moment arms, 6 and 7. If, for example, beam moment arm, 6, were to be made half of the length of moment arm, 7, then the weight of body, 1, would have to be doubled to maintain balance. Doubling this weight would mean doubling its volume, if its density were to be kept unchanged. Doubling the volume will double the buoyant force which will exactly balance half the buoyant force on body, 2, since body, 2, has double the moment arm. Changing the balance arm ratio, then, will not affect any final resulting torque generated by fluid density.

Lastly, the buoyancy effect can also be obtained by using different geometrical configurations for bodies, 1 and 2. Using this approach, body, 2, could be made in the form of a sphere and body, 1, could be a cylinder. Since a given mass occupies the lowest possible volume in the shape of a sphere then the buoyancy force of body, 1, will be larger. Alternately, body, 1, could be constructed as a completely sealed pressure vessel, which is void on the inside. These approaches will also result in unequal buoyancies and a torque proportional to fluid density.

The basic arrangement outlined in FIG. 1 does not directly lend itself to deployment within a well bore because of the inherent dimensional restrictions imposed by the well diameter. Hence, the masses, 1 and 2 of FIG. 1 will necessarily have to be aligned with the axis of the well bore to be able to generate enough buoyancy effect to be useful so this would require the balance shaft 4 to be at right angles with the bore axis. The torque sensor and required electronics, however, must also be aligned with the well bore because of the same dimensional restrictions. This, them, requires that the torque T1 must somehow make a right angle turn to drive a torque sensor. Right angle gears and such are normally used to address this type of situation but these conventional approaches will not provide the accuracy or lack of friction required by this application.

Figure 2A:
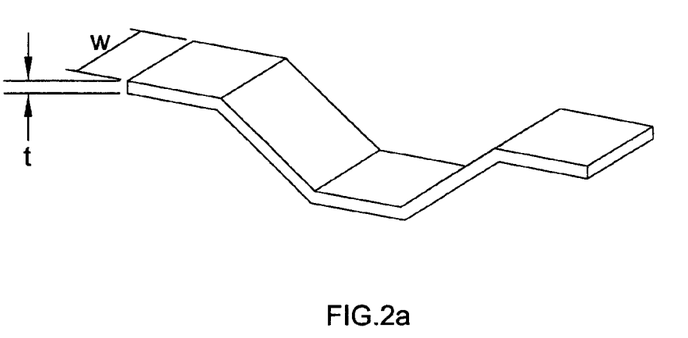
FIG. 2 is an illustration of the linkage used to convert axial force into sensor shaft torque.
Figure 2B:
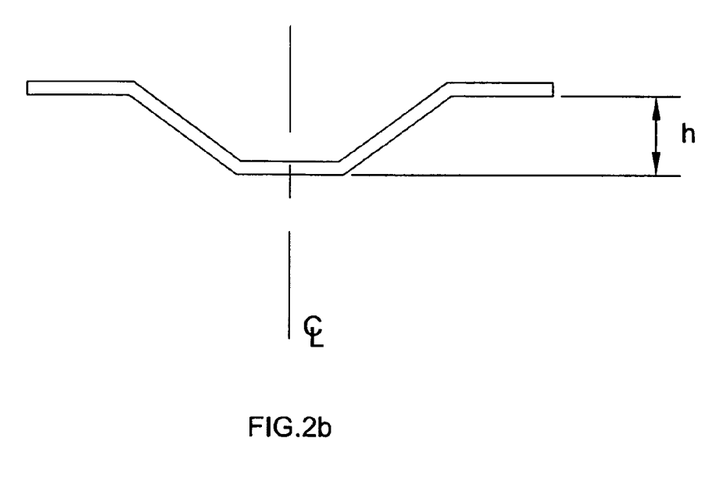

FIG. 2a depicts a linkage which is used to accomplish this function and FIG. 2b is side view of the same linkage. Generally, the linkage is symmetrical about the centerline of 2b and height dimension, h, is also the same on both sides of the centerline. The dimensions of the linkage, including the thickness, t, and width, w, of 2a are chosen to allow small flexures of all of the angles by relatively small forces with respect to the mass forces to be measured.

Figure 3:
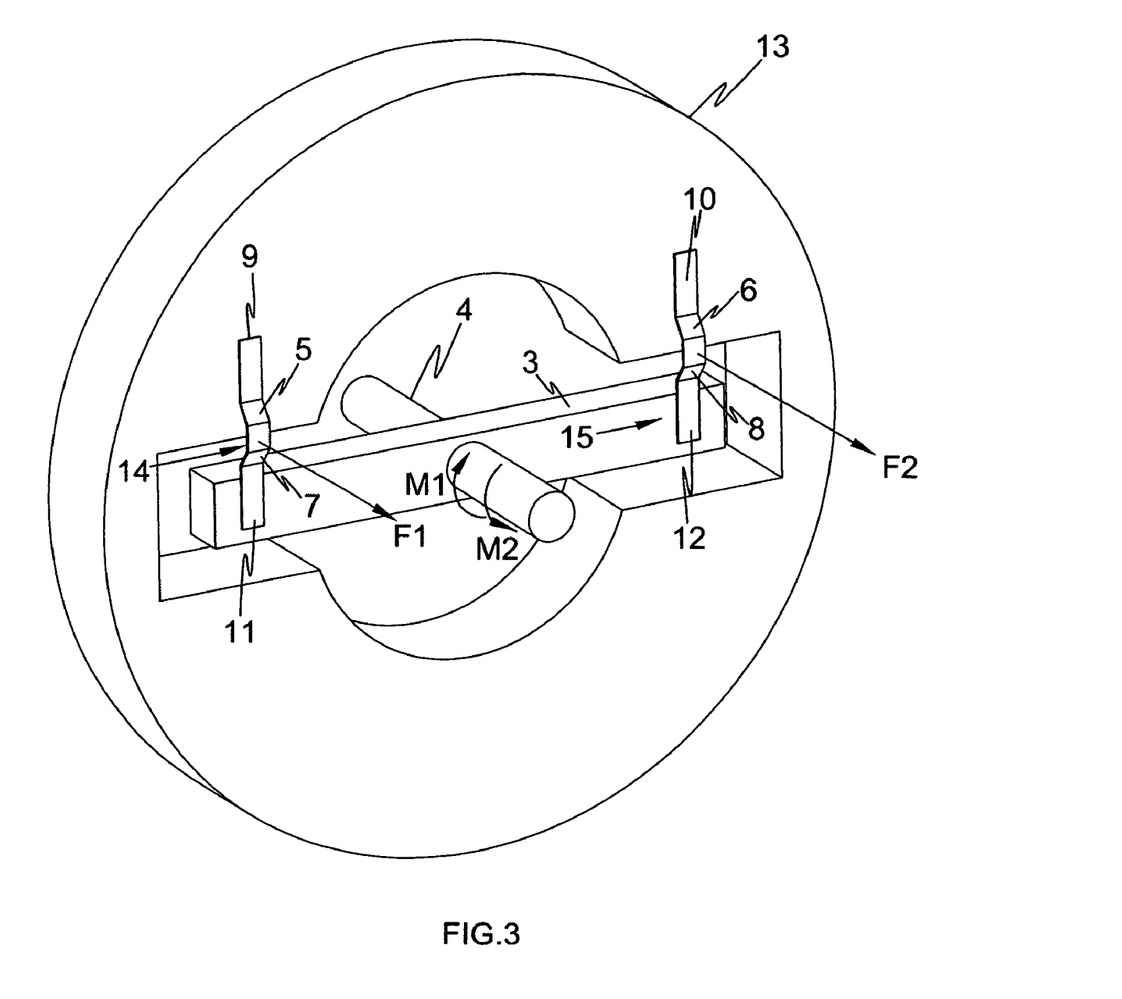
FIG. 3 illustrates the right angle coupling in detail.

FIG. 3 depicts how the linkage of FIG. 2 is configured to accomplish the right angle torque function. Two linkages, 14 and 15, are used together with a balance beam 3 which is attached to an output torque shaft 4. The function of linkages, 14 and 15, is to convert the force of parallel, axially aligned force vectors, F1 and F2 (from float masses 1 and 2, not shown) into moments, M1 and M2, respectively. The linkages do this by virtue of each having one leg, 5 and 6, anchored to the partition section 13 of pressure housing 17, at points 9 and 10, with their opposite legs, 7 and 8, attached to the torque balance beam 3 at points 11 and 12. This arrangement will produce opposing moments, M1 and M2, and therefore opposing torques, in the torque output shaft 4. Positive and negative torques are produced, then, just as in the case of the balance beam of FIG. 1. This result means that the torque applied to the torque sensor is essentially free of the effects of vibration or other external forces common to both float mass forces, F1 and F2.

Figure 4:
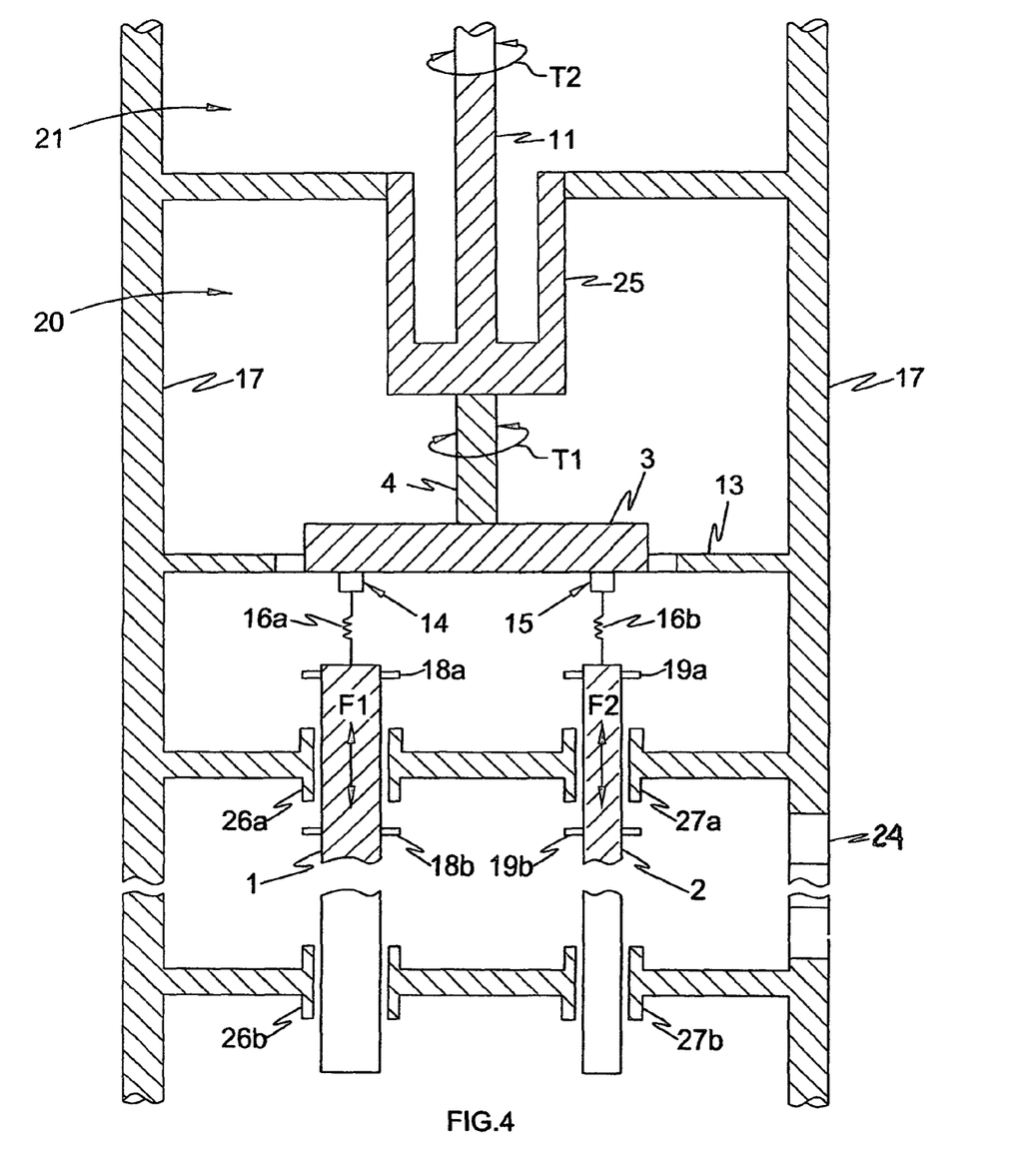
FIG. 4 is an illustration of the entire density sensor for the first embodiment.

FIG. 4 depicts an entire sensor assembly mounted within a pressure housing, 17, which is ported to outside well fluids by port, 24. The components of FIG. 3 have been incorporated in FIG. 4 to provide the required force-to-torque conversion to drive output torque T1. Thus, the torque shaft 4 and balance beam 3 of FIG. 3 are also shown as items 4 and 3 in FIG. 4. This is also true for linkages, 14 and 15, as well as the section 13 of the pressure housing 17 that anchors the linkages.

Additional features of a pressure isolation tube, 25, and immersion body support springs, 16a and 16b, have also been added. The pressure isolation tube will be discussed below. The immersion body support springs, 16a and 16b, function together with travel stops, 18a and b thru 19 a and b, to limit torque, T1, output under overload conditions of the float masses, 1 and 2. Substantial overloads can easily occur in a well bore environment because of shock, vibration or flow conditions. If the springs, 16a and 16b, were not present then these overload forces would be applied directly to the torque sensor because of the very small operating displacement of the sensor assembly. This displacement would be so small that the overload stops could not be effective so this situation is addressed by the force/displacement characteristics of springs, 16a and 16b. These are simply chosen so that the force necessary to displace them to a travel stop creates an output torque, T2, which is within the torque capability of the torque sensor.

FIG. 4 also shows the float masses, 1 and 2, to be guided by bushings, 26 a and b and 27 a and b. A spring suspension for these masses could be devised to eliminate the effects of friction but these bushings have the advantage of being rugged while also having no effect on the measurement once friction is overcome. Friction effects can be largely eliminated by using low friction materials, such as polytetrafluoroethylene (Teflon®), for this purpose. Moreover, the motion and vibration effects which are normal during deployment will serve to 'dither' out any remaining friction effects.

Figure 5:
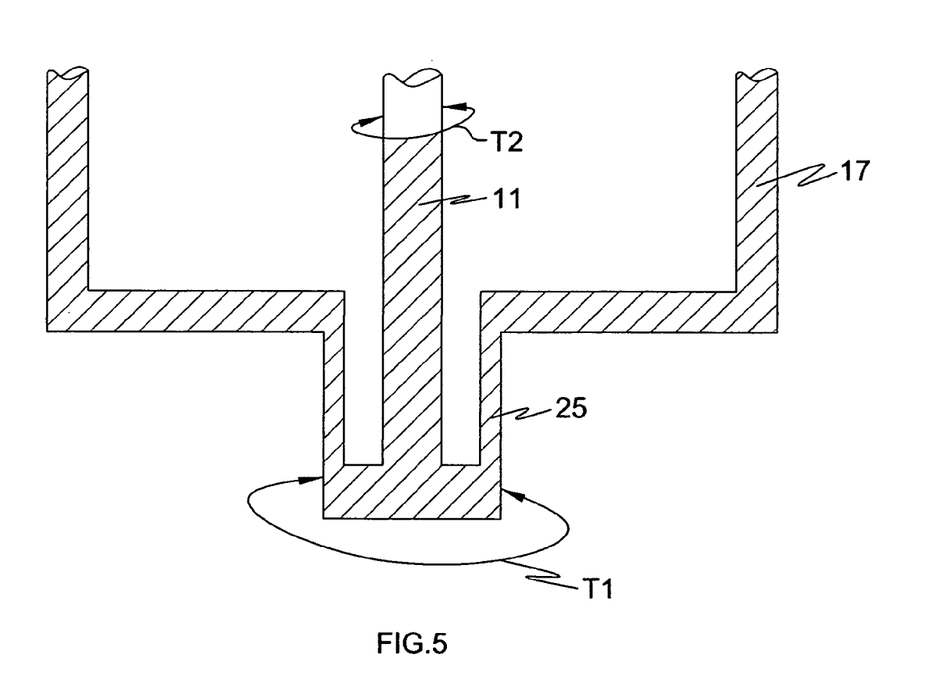
FIG. 5 is an illustration of a pressure isolator torque tube.

FIG. 5 depicts the pressure isolation torque tube, 25, used in FIG. 4 to couple the output torque of the density sensor from a high pressure well fluid environment, 20, (FIG. 4) to a more accommodating, non-corrosive environment, of chamber 21. It consists of a closed end tube 25 which is non-rotatively anchored and sealed at its open end to the pressure housing 17. A torque shaft, 11, is non-rotatively secured to the torque tube 25 base and extended coaxially within the tube so that an applied torque, T1, at its base, will also couple to the shaft 11. By "non-rotatively" anchored or secured, it is meant that any angular displacement of the shaft, however minute, about the axis of shaft 4 is torsional strain due only to torsional stress. The pressure isolation tube, 25, encloses and isolates shaft, 11, and any associated instrumentation, from well fluids surrounding its exterior. The effects of pressure and temperature are to change linear dimensions of the pressure isolator tube but neither of these will materially affect torsional forces. Torque, then, is transmitted from, T1, to, T2, (in both FIGS. 4 and 5) without friction or any adverse effects normally produced by pressure seals.

Figure 6:
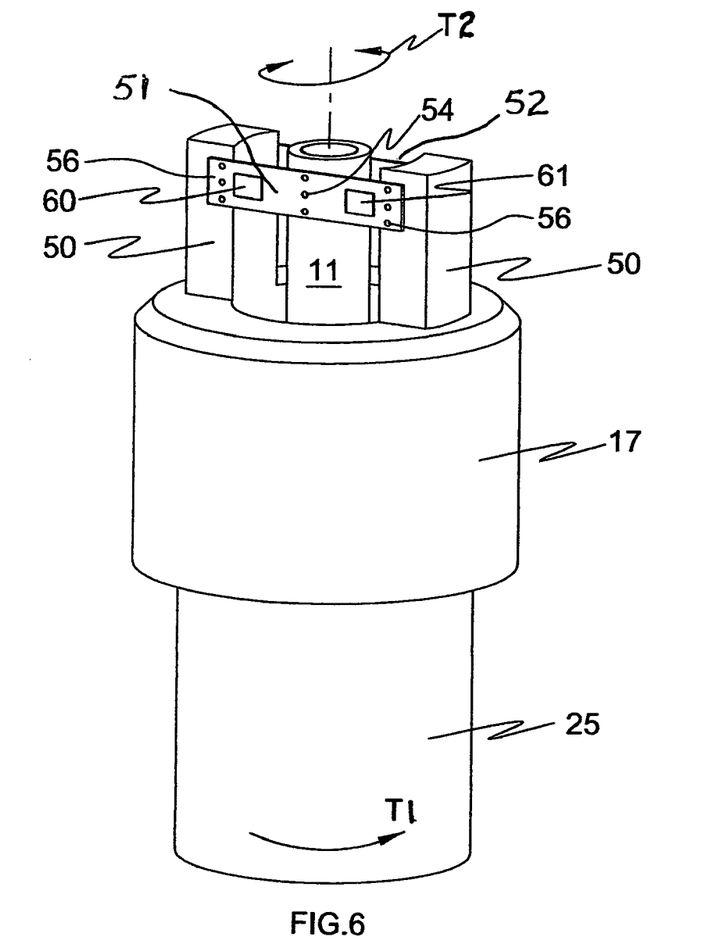
FIG. 6 is an illustration of the strain gauge mounting structure for measuring torque.
Figure 7:
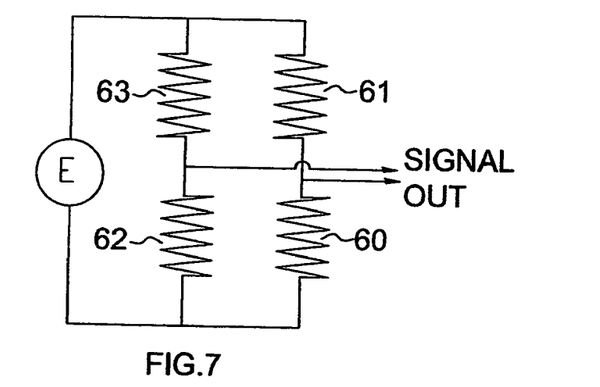
FIG. 7 is an illustration of the position of each strain gauge within a bridge circuit.

The angular displacement of shaft 11 imposed by the torsional stress $T_1$ on the pressure isolation tube 25 may be calibrated to a proportioned relationship with the density related torque T1 of torque shaft 4 in FIG. 4. There are numerous methods of measuring such a minute angular displacement. Among the more practical methods applicable to a down hole well environment are electrical sensors based upon capacitive and piezoresistive property changes. Suitable capacitive measuring instruments are disclosed in U.S. Pat. No. 5,463,903, the specification of which is hereby incorporated by reference. A piezoresistive means for translating the minute angular displacements of shaft 11 is represented by FIGS. 6 and 7.

Figure 8:
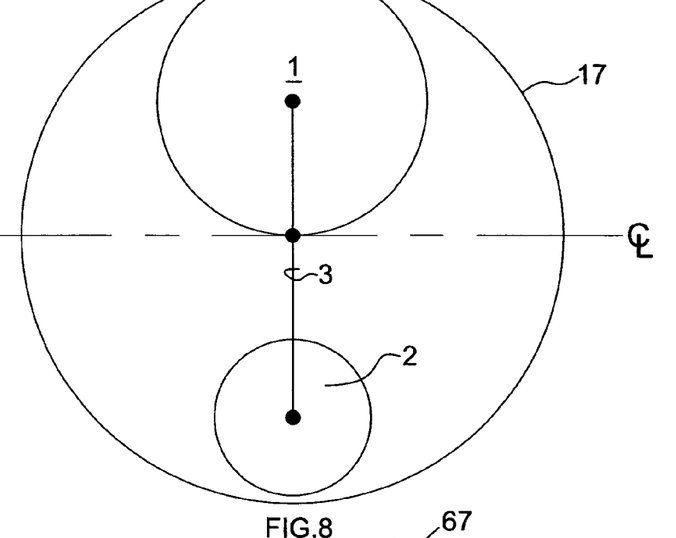
FIG. 8 is a top schematic view of the immersion bodies mounted within a pressure vessel.

The primary sensing element of a piezoresistive instrument is commonly characterized as a strain gauge. FIG. 6 illustrates the basic strain gauge mounting configuration of this invention which shows the wall of the pressure isolation tube 25 attached to the pressure housing 17 at an open end. Also secured to the housing 17 are a pair of diametrically aligned anchor posts 50 in flanking symmetry with an extend portion of the shaft 11. The pressure isolation tube shaft, 11, is attached, at 54, to the midpoints of two strain gauge substrates 51 and 52 comprising thin beams. Representatively, the substrate beams 51 and 52 may be thin strips of stainless steel foil. The substrate beams 51 and 52 are attached to the shaft 11 at its diametrically opposite tangent points 54 by spot welding, for example. Also, the respective ends of these beams 51 and 52 are similarly attached at 56 to anchor posts 50 so that any angular displacement due to torque T2, will result in tensile and compressive forces within the beam halves of 51 and 52. These forces are then sensed by strain gauges 60 and 61 on beam 51 and gauges 62 and 63 on beam 52, (FIG. 7) which are applied intimately to the surface of substrate beams 51 and 52 by a suitable bonding agent such as epoxy. The strain gauges 60, 61, 62 and 63 are electrically connected to form the four legs of a full bridge circuit. This circuit is shown in FIG. 8. Each of the gauges, then, will respond with a change in electrical resistance properties to strain induced by and angular displacement of the shaft 11. A corresponding electrical signal at the bridge circuit output is produced.

Referring again to FIG. 4, an imbalance in the axial forces produced by immersion bodies, 1 and 2, will result in torque T1 within the pivot shaft, 4, (just as in FIG. 1, with the same designator numbers). This torque T1 is coupled by tubular member, 4, to the base of tubular member 25 (FIG. 6). Torque T1 is then transmitted to shaft 11 to become angular displacement T2 as shown in FIGS. 4, 5 and 6. It should be understood that the angular displacement T2 is extremely minute and revealed only by sensitive measurement.

As shown in FIG. 4, a pressure housing designed for well bore deployment is normally configured in a long, cylindrical form. This shape, then, requires the immersion bodies, 1 and 2, to be long cylindrical rods. An end view of this arrangement is shown in FIG. 8.

Referring to FIG. 3, the moment arm for each float mass force is simply its distance to the center of the balance beam. FIG. 8 illustrates the limitations imposed by the maximum outside diameter of the pressure housing. As in the other figures, the balance beam in FIG. 8 is designated by, 3. Immersion bodies, 1 and 2, are supported at their center of mass and the ratio of their diameters is determined by their relative densities, if they are equal in length. It should be noted that the acting mass force of any body must always pass through its center of mass so supporting the bodies at another point will not change the magnitude of their conversion to torque. Also, the maximum available moment exists when body, 1, completely fills half of the available space but the moment arm to the center of mass will only be half of the radius. This dimensional limitation, then, limits the size of the float masses to only a fraction of the available volume within the pressure housing.

Figure 9:
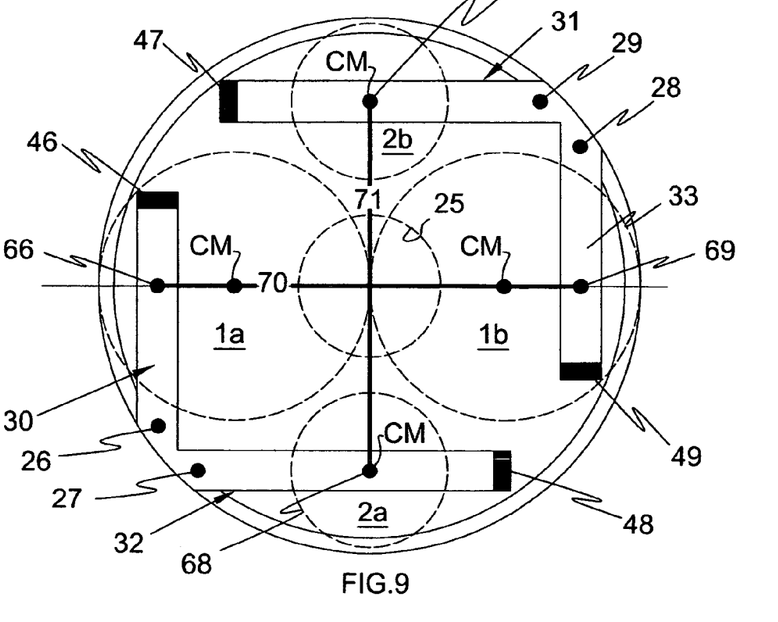
FIG. 9 is a top schematic view of the immersion bodies as configured for a second embodiment of the invention.

Another approach for mounting the immersion bodies is shown in FIG. 9. This consists of using two sets of immersion bodies, in a push-pull arrangement, to create a pure torque output with no lateral loading of the output shaft and therefore no lateral compliance restriction. This arrangement also results in immersion bodies, 1*a* and 1*b*, fully occupying one half of the area of pressure vessel, 17, with an effective moment arm of fully half of the diameter of immersion body, 1, of FIG. 3. What is needed is a way to be able to vary the position of the float body center of mass without affecting the effective moment arm.

Figure 10:
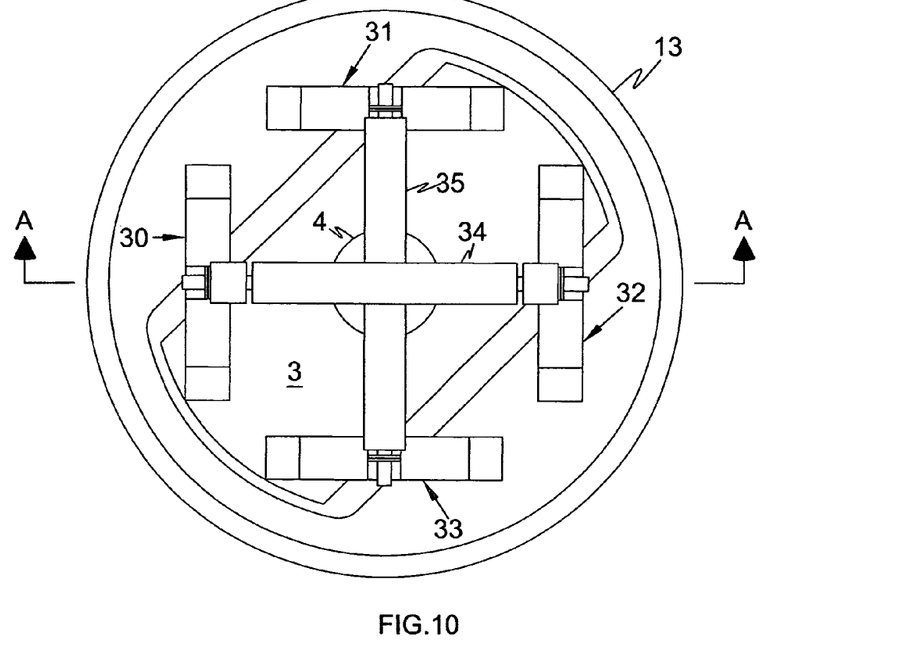
FIG. 10 is a perspective illustration of the principles of a second embodiment of the invention.

FIG. 10 is an illustration of a second embodiment which has this feature. This figure is similar to FIG. 3 except that it is not presented as an isometric view. There are three major differences, however, between the two approaches. The first is that FIG. 3 utilizes two linkages (14 and 15) of the FIG. 2 type while four are utilized in FIG. 10 (30, 31, 32 and 33). The second difference is that the linkages are paired into two pairs (30 and 32; 31 and 33) with each pair member facing the other at 180 degrees. Each pair also is mounted to give the same moment direction and then they are strapped together with a rod (34 and 35). Each rod, then, can have more than one float mass suspended from it as long as they are the same type (float mass 1 or float mass 2). This allows the float mass centers to be at any position on the rod (preferably symmetrically with respect to the center) and still have the same moment arm effect on the output torque. The last major difference between the first and second embodiment is that the output torque shaft 4 always sees pure torque forces in FIG. 10 whereas the torque output shaft 4 of FIG. 3 will experience lateral forces which are unbalanced. This occurs in FIG. 3 because canceling moments M1 and M2 are each developed on only one side of the balance beam 3. In the arrangement of FIG. 10, however, each moment is applied equally on both sides of the balance beam 3 (if the float mass pairs are matched) so that pure torque results with no unbalanced lateral forces.

Figure 11:
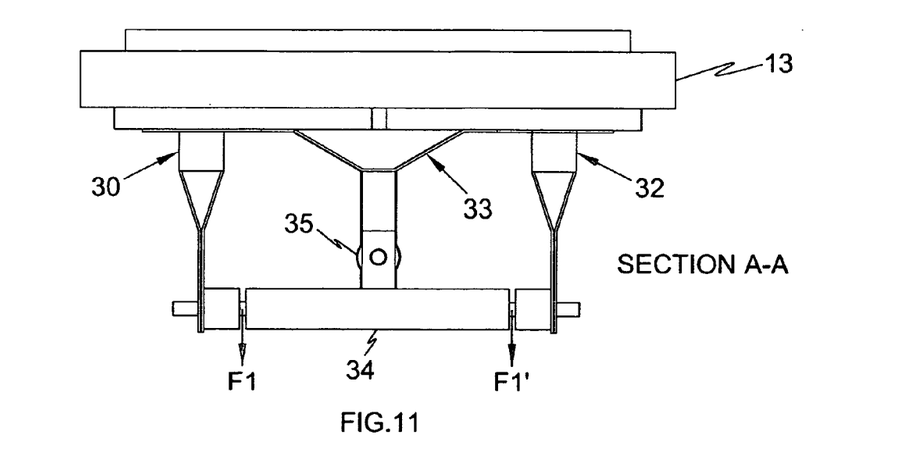
FIG. 11 is a partial sectional view of FIG. 10 taken along cutting plane A-A to further illustrate principles of the second embodiment.

FIG. 11, depicts section A-A of FIG. 10. As can be seen, linkages, 30 and 32, are paired at 180 degrees and coupled together by shaft 34. Cloned float masses, 1 and 1', are suspended from the shaft 34 at the positions occupied by their resulting forces, F1 and F1', as shown. Since these forces are supported symmetrically, with respect to the center of shaft 34, then half of the sum will appear at each linkage, 30 and 32. It is apparent that this relationship will hold even if the points of force application are moved symmetrically.

FIG. 9, illustrates an end view of the float masses for the second embodiment, similar to the view of FIG. 8. The four linkages, 30, 31, 32 and 33, are depicted, for purposes of illustration, with one end extended to an anchor point on the pressure housing. These anchor points are 26, 27, 28 and 29. The ends of each linkage which are attached to the balance beam are shown with a heavy dark band and these are 46, 47, 48 and 49. Also, the two linkage connecting rods, 70 and 71 are shown connected to the linkages at 66, 67, 68 and 69. The large float masses, 1*a* and 1*b*, are connected to rod 70 at their center of mass, designated as CM while the two smaller float masses, 2*a* and 2*b*, have their center of mass connected directly to linkages 31 and 33. The position of the output torque shaft 25 is also shown for reference. It is apparent, in this arrangement, that nearly the entire circular volume of the pressure housing is actively utilized for the float masses as opposed to the very poor utilization of FIG. 8.

This second embodiment achieves all of the objectives of being a densitometer compatible for deployment within a well bore as well as having a true differential torque output representative of the differences of floatation between two different, acceleration balanced, immersed bodies.

It will be apparent to those skilled in the art that various changes may be made in the invention without departing from the spirit and scope thereof and therefore the invention is not limited by that which is disclosed in the drawings and specifications but only as indicated in the appended claims. Although the value described by the foregoing specification has been characterized as "density", those of ordinary skill understand that "specific gravity" is the mathematical reciprocal of "density. Hence, the value "specific gravity" may be substituted herein for all references to "density".

Although the invention disclosed herein has been described in terms of specified and presently preferred embodiments which are set forth in detail, it should be understood that this is by illustration only and that the invention is not necessarily limited thereto. Alternative embodiments and operating techniques will become apparent to those of ordinary skill in the art in view of the present disclosure. Accordingly, modifications of the invention are contemplated which may be made without departing from the spirit of the claimed invention.

The invention claimed is:

1. A fluid density measuring apparatus comprising:
   a first mass having a first weight and a first volume;
   a second mass having a second weight and second volume, said first weight being substantially the same as said second weight and said first volume being greater than said second volume;
   a first torque shaft having a longitudinal axis secured non-rotatively to a housing structure;

a first balance beam non-rotatively secured to said first torque shaft with respective moment arms extending in opposite directions from said first torque longitudinal shaft axis;

first and second links secured at one respective end to a respective moment arm and another end to said housing structure, said first and second masses suspended from respective links between said ends;

coupling means non-rotatively secured to said first torque shaft for translating torsional displacement of said first torque shaft to angular displacement of a first torsional element about said longitudinal axis;

electrical sensing means for converting said angular displacement of said first torsional element to a proportional change in an electrical property; and, means for translating said electrical property change to a value corresponding to a density of a fluid in which said masses are immersed.

2. A fluid density measuring apparatus as describe by claim 1 wherein said electrical sensing means comprises strain gauges.

3. A fluid density measuring apparatus as described by claim 1 further comprising third and forth masses having substantially the same properties as said first and second masses, said third and forth masses being suspended from respective links between said housing structure and respective moment arms of said balance beam.

4. A fluid density measuring apparatus as described by claim 3 wherein said coupling means comprises a pressure isolation cylinder between said first torque shaft and said housing structure.

5. A fluid density measuring apparatus as described by claim 1 wherein said electrical sensing means is environmentally isolated from said fluid in which said masses are immersed.

6. A fluid density measuring apparatus comprising:

a first mass having a first weight and a first volume;

a second mass having a second weight and second volume, said first weight being substantially the same as said second weight and said first volume being greater than said second volume;

first and second links respectively suspending said first and second masses along substantially parallel vector directions of weight force, one end of each link secured to a housing and an opposite end of each link secured to a torsion coupling, said torsion coupling having a torque axis aligned substantially parallel with said weight force vector direction;

electrical sensing means for converting angular displacement of said coupling about said torque axis to a proportional change in an electrical property; and, means for translating said electrical property change to a value corresponding to a density of a fluid in which said masses are immersed.

7. A fluid density measuring apparatus as describe by claim 6 wherein said electrical sensing means comprises strain gauges.

8. A fluid density measuring apparatus as describe by claim 6 further having third and fourth masses substantially corresponding to said first and second masses; third and fourth links respectfully suspending said third and fourth masses, said third and fourth links each having one end secured to said housing and an opposite end secured to said torsion coupling.

9. A fluid density measuring apparatus as describe by claim 6 wherein said electrical sensing means is environmentally isolated from said fluid in which said masses are immersed.

10. A method of measuring a fluid density comprising the steps of:

providing at least a pair of masses, each mass having weight substantially equal to the other but substantially unequal buoyancy;

suspending said masses in a fluid on opposite sides of a first torque axis, directional vectors of said mass weight aligned substantially parallel with said torque axis;

generating a torsional force about said axis by a buoyancy differential between said masses;

converting said torsional force to an angular displacement about said torque axis;

altering an electrical property in proportion to said angular displacement; and, translating said electrical property alteration to a density value of said fluid.

11. A method of measuring a fluid density as described by claim 10 wherein at least two pairs of masses are suspended in said fluid with opposite members of each pair suspended on opposite sides of said torque axis.

12. A method of measuring a fluid density as described by claim 10 wherein said masses are suspended from respective links between respective distal ends thereof, one end of each link being secured to a housing element and the other end of each link being secured to a means for converting said torsional force to an angular displacement about a torque axis.

13. A method of measuring a fluid density as described by claim 10 wherein said masses are immersed in a first fluid environment.

14. A method of measuring a fluid density as described by claim 13 wherein said electrical property alteration and translation occurs in a second environment isolated from said first environment.

15. An apparatus for measuring the density of a fluid comprising: at least first and second masses having equal weight and unequal volume, first and second links secured at one end thereof to a tubular housing and at another end thereof to a torsion beam, said torsion beam having a torque axis substantially parallel with an axis of said tubular housing, said first and second masses, respectively, suspended from said links at a point between said ends, a torque shaft secured to said torque beam and to extend along said torque axis, a sensor responsive to angular displacement of said torque shaft to change an electrical property and calibrated translation means to convert said electrical property change to a density value of a fluid in which said masses are immersed.

16. An apparatus for measuring the density of a fluid as described by claim 15 wherein said sensor comprises strain gauges.

17. An apparatus for measuring the density of a fluid as described by claim 15 wherein said sensor is environmentally isolated from said fluid in which said masses are immersed.

18. An apparatus for measuring the density of a fluid as described by claim 15 further having third and fourth masses substantially corresponding to said first and second masses; said third and fourth masses respectively suspended from third and fourth links having ends thereof secured to said torsion beam and said tubular housing.

* * * * *